United States Patent
Poppe et al.

(10) Patent No.: US 11,723,767 B2
(45) Date of Patent: Aug. 15, 2023

(54) MEDICAL DEVICE INCLUDING ATTACHABLE TIP MEMBER

(71) Applicant: BOSTON SCIENTIFIC SCIMED, INC., Maple Grove, MN (US)

(72) Inventors: Kevin Robert Poppe, New Brighton, MN (US); Daniel J. Foster, Lino Lakes, MN (US); Christopher Jay Scheff, Elk River, MN (US); Bradley S. Swehla, Eagan, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 155 days.

(21) Appl. No.: 16/992,597

(22) Filed: Aug. 13, 2020

(65) Prior Publication Data

US 2021/0045873 A1 Feb. 18, 2021

Related U.S. Application Data

(60) Provisional application No. 62/887,088, filed on Aug. 15, 2019.

(51) Int. Cl.
*A61F 2/24* (2006.01)
*A61M 25/00* (2006.01)

(52) U.S. Cl.
CPC ....... *A61F 2/2436* (2013.01); *A61M 25/0068* (2013.01); *A61M 25/0082* (2013.01); *A61M 2025/0096* (2013.01)

(58) Field of Classification Search
CPC ............. A61F 2/2436; A61M 25/0068; A61M 25/0082; A61M 2025/0096
See application file for complete search history.

(56) References Cited

U.S. PATENT DOCUMENTS 3,674,014 A 7/1972 Tillander
4,798,598 A 1/1989 Bonello et al.
(Continued)

FOREIGN PATENT DOCUMENTS

EP 0778040 A2 6/1997
EP 1168986 A1 1/2002
(Continued)

OTHER PUBLICATIONS

International Search Report and Written Opinion dated Mar. 2, 2018 for International Application No. PCT/US2017/062113.
(Continued)

*Primary Examiner* — Thomas McEvoy
(74) *Attorney, Agent, or Firm* — Seager, Tufte & Wickhem LLP

(57) ABSTRACT

Medical device delivery systems and methods for making and using medical device delivery systems are disclosed. An example delivery system for an implantable medical device includes an implantable heart valve including an inner shaft having a proximal end region, a distal end region and a first engagement member disposed along a portion of the distal end region and a tip assembly configured to attach to the inner shaft. The tip assembly includes a nosecone having a distal end region and a proximal end region, a second engagement member disposed within at least a portion of the nosecone, the second engagement member including a first locking member, the first locking member configured to deflect from a first position to a second engaged position. Further, attaching the tip assembly to the inner shaft includes deflecting the first locking member such that the locking member is coupled to the first engagement member.

19 Claims, 11 Drawing Sheets

(56) References Cited

U.S. PATENT DOCUMENTS

| | | |
|---|---|---|
| 4,955,384 A | 9/1990 | Taylor et al. |
| 4,985,022 A | 1/1991 | Fearnot et al. |
| 4,998,923 A | 3/1991 | Samson et al. |
| 5,003,989 A | 4/1991 | Taylor et al. |
| 5,095,915 A | 3/1992 | Engelson |
| 5,315,996 A | 5/1994 | Lundquist |
| 5,406,960 A | 4/1995 | Corso, Jr. |
| 5,437,288 A | 8/1995 | Schwartz et al. |
| 5,570,701 A | 11/1996 | Ellis et al. |
| 5,599,492 A | 2/1997 | Engelson |
| 5,746,701 A | 5/1998 | Noone |
| 5,749,837 A | 5/1998 | Palermo et al. |
| 5,769,796 A | 6/1998 | Palermo et al. |
| 5,772,609 A | 6/1998 | Nguyen et al. |
| 5,776,080 A | 7/1998 | Thome et al. |
| 5,833,632 A | 11/1998 | Jacobsen et al. |
| 5,902,254 A | 5/1999 | Magram |
| 5,931,830 A | 8/1999 | Jacobsen et al. |
| 5,951,494 A | 9/1999 | Wang et al. |
| 6,001,068 A | 12/1999 | Uchino et al. |
| 6,017,319 A | 1/2000 | Jacobsen et al. |
| 6,139,510 A | 10/2000 | Palermo |
| 6,273,876 B1 | 8/2001 | Klima et al. |
| 6,606,921 B2 | 8/2003 | Noetzold |
| 6,739,787 B1 | 5/2004 | Bystrom |
| 6,918,882 B2 | 7/2005 | Skujins et al. |
| 6,921,397 B2 | 7/2005 | Corcoran et al. |
| 7,055,656 B2 | 6/2006 | Drew |
| 7,074,197 B2 | 7/2006 | Reynolds et al. |
| 7,338,495 B2 | 3/2008 | Adams |
| 7,413,563 B2 | 8/2008 | Corcoran et al. |
| 7,533,906 B2 | 5/2009 | Luettgen et al. |
| 7,540,865 B2 | 6/2009 | Griffin et al. |
| 7,579,550 B2 | 8/2009 | Dayton et al. |
| 7,618,379 B2 | 11/2009 | Reynolds et al. |
| 7,625,364 B2 | 12/2009 | Corcoran et al. |
| 7,780,611 B2 | 8/2010 | Griego et al. |
| 7,784,376 B2 | 8/2010 | Wen |
| 7,824,345 B2 | 11/2010 | Euteneuer et al. |
| 7,841,994 B2 | 11/2010 | Skujins et al. |
| 7,850,623 B2 | 12/2010 | Griffin et al. |
| 7,854,109 B2 | 12/2010 | Zubiate et al. |
| 7,914,466 B2 | 3/2011 | Davis et al. |
| 7,914,467 B2 | 3/2011 | Layman et al. |
| 7,918,080 B2 | 4/2011 | Zubiate et al. |
| 7,993,286 B2 | 8/2011 | Reynolds et al. |
| 8,022,331 B2 | 9/2011 | Reynolds et al. |
| 8,047,236 B2 | 11/2011 | Perry |
| 8,048,004 B2 | 11/2011 | Davis et al. |
| 8,048,060 B2 | 11/2011 | Griffin et al. |
| 8,099,939 B2 | 1/2012 | Zubiate et al. |
| 8,100,031 B2 | 1/2012 | Zubiate et al. |
| 8,105,246 B2 | 1/2012 | Voeller et al. |
| 8,124,876 B2 | 2/2012 | Dayton et al. |
| 8,137,293 B2 | 3/2012 | Zhou et al. |
| 8,157,751 B2 | 4/2012 | Adams et al. |
| 8,182,465 B2 | 5/2012 | Griffin et al. |
| 8,192,422 B2 | 6/2012 | Zubiate et al. |
| 8,197,419 B2 | 6/2012 | Field et al. |
| 8,231,551 B2 | 7/2012 | Griffin et al. |
| 8,257,279 B2 | 9/2012 | Davis et al. |
| 8,292,829 B2 | 10/2012 | Griego et al. |
| 8,317,777 B2 | 11/2012 | Zubiate et al. |
| 8,376,865 B2 | 2/2013 | Forster et al. |
| 8,376,961 B2 | 2/2013 | Layman et al. |
| 8,377,035 B2 | 2/2013 | Zhou et al. |
| 8,397,481 B2 | 3/2013 | Zubiate et al. |
| 8,409,114 B2 | 4/2013 | Parins |
| 8,414,506 B2 | 4/2013 | Reynolds et al. |
| 8,425,408 B2 | 4/2013 | Boulais et al. |
| 8,443,692 B2 | 5/2013 | Zubiate et al. |
| 8,449,526 B2 | 5/2013 | Snyder et al. |
| 8,459,138 B2 | 6/2013 | Zubiate et al. |
| 8,475,366 B2 | 7/2013 | Boulais et al. |
| 8,485,992 B2 | 7/2013 | Griffin et al. |
| 8,535,219 B2 | 9/2013 | Smith et al. |
| 8,535,243 B2 | 9/2013 | Shireman |
| 8,551,020 B2 | 10/2013 | Chen et al. |
| 8,551,021 B2 | 10/2013 | Voeller et al. |
| 8,556,914 B2 | 10/2013 | Vrba |
| 8,608,648 B2 | 12/2013 | Banik et al. |
| 8,622,894 B2 | 1/2014 | Banik et al. |
| 8,636,716 B2 | 1/2014 | Griffin et al. |
| 8,656,697 B2 | 2/2014 | Zubiate et al. |
| 8,677,602 B2 | 3/2014 | Dayton et al. |
| 8,758,268 B2 | 6/2014 | Bown et al. |
| 8,784,337 B2 | 7/2014 | Voeller et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,833,197 B2 | 9/2014 | Zubiate et al. |
| 8,845,552 B2 | 9/2014 | Griego et al. |
| 8,864,654 B2 | 10/2014 | Kleiner et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,945,096 B2 | 2/2015 | Zubiate et al. |
| 9,005,114 B2 | 4/2015 | Zubiate et al. |
| 9,011,318 B2 | 4/2015 | Choset et al. |
| 9,023,011 B2 | 5/2015 | Griffin et al. |
| 9,072,874 B2 | 7/2015 | Northrop et al. |
| 9,370,432 B2 | 6/2016 | Bennett et al. |
| 9,375,234 B2 | 6/2016 | Vrba |
| 9,386,911 B2 | 7/2016 | Zubiate et al. |
| 9,387,308 B2 | 7/2016 | Hinchliffe et al. |
| 9,387,309 B2 | 7/2016 | Parodi et al. |
| 9,402,682 B2 | 8/2016 | Worrell et al. |
| 2001/0037141 A1 | 11/2001 | Yee et al. |
| 2003/0069520 A1 | 4/2003 | Skujins et al. |
| 2003/0069521 A1 | 4/2003 | Reynolds et al. |
| 2004/0220499 A1 | 11/2004 | Griego et al. |
| 2004/0243143 A1 | 12/2004 | Corcoran et al. |
| 2005/0080400 A1 | 4/2005 | Corcoran et al. |
| 2005/0090848 A1 | 4/2005 | Adams |
| 2005/0267444 A1 | 12/2005 | Griffin et al. |
| 2006/0111615 A1 | 5/2006 | Danitz et al. |
| 2006/0122537 A1 | 6/2006 | Reynolds et al. |
| 2006/0179966 A1 | 8/2006 | Kuo |
| 2006/0189896 A1 | 8/2006 | Davis et al. |
| 2007/0049902 A1 | 3/2007 | Griffin et al. |
| 2007/0066900 A1 | 3/2007 | O'Keeffe |
| 2007/0083132 A1 | 4/2007 | Sharrow |
| 2007/0100285 A1 | 5/2007 | Griffin et al. |
| 2007/0114211 A1 | 5/2007 | Reynolds et al. |
| 2007/0135734 A1 | 6/2007 | Reynolds et al. |
| 2007/0233043 A1 | 10/2007 | Dayton et al. |
| 2007/0244414 A1 | 10/2007 | Reynolds et al. |
| 2007/0265637 A1 | 11/2007 | Andreas et al. |
| 2008/0064989 A1 | 3/2008 | Chen et al. |
| 2008/0077119 A1 | 3/2008 | Snyder et al. |
| 2008/0194994 A1 | 8/2008 | Bown et al. |
| 2008/0205980 A1 | 8/2008 | Zubiate et al. |
| 2008/0245173 A1 | 10/2008 | Schwerin et al. |
| 2008/0255655 A1 | 10/2008 | Kusleika et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0143768 A1 | 6/2009 | Parodi et al. |
| 2009/0156999 A1 | 6/2009 | Adams et al. |
| 2009/0163915 A1* | 6/2009 | Potter ............... A61M 25/0147 606/41 |
| 2009/0171151 A1 | 7/2009 | Choset et al. |
| 2009/0312606 A1 | 12/2009 | Dayton et al. |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0234933 A1 | 9/2010 | Punga et al. |
| 2010/0249655 A1 | 9/2010 | Lemon |
| 2010/0286566 A1 | 11/2010 | Griffin et al. |

(56) References Cited

U.S. PATENT DOCUMENTS

| | | |
|---|---|---|
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0178588 A1 | 7/2011 | Haselby |
| 2011/0184241 A1 | 7/2011 | Zubiate et al. |
| 2011/0257478 A1 | 10/2011 | Kleiner et al. |
| 2011/0264191 A1 | 10/2011 | Rothstein |
| 2012/0160537 A1 | 6/2012 | Wen |
| 2013/0123796 A1 | 5/2013 | Sutton et al. |
| 2013/0123912 A1 | 5/2013 | Tung et al. |
| 2013/0144276 A1 | 6/2013 | Crisostomo et al. |
| 2014/0235361 A1 | 8/2014 | Forster et al. |
| 2016/0317301 A1 | 11/2016 | Quadri et al. |
| 2018/0140323 A1 | 5/2018 | Foster et al. |
| 2019/0298557 A1* | 10/2019 | Murray, III ........... A61F 2/2436 |

FOREIGN PATENT DOCUMENTS

| | | |
|---|---|---|
| EP | 1707136 A1 | 10/2006 |
| EP | 2455128 A2 | 5/2013 |
| JP | 5575840 B2 | 8/2014 |
| WO | 0061035 A1 | 10/2000 |
| WO | 2006041612 A2 | 4/2006 |
| WO | 2006073581 A2 | 7/2006 |
| WO | 2011133486 A1 | 10/2011 |
| WO | 2017035381 A1 | 3/2017 |
| WO | 2017210466 A1 | 12/2017 |
| WO | 2018170092 A1 | 9/2018 |
| WO | 2018204558 A1 | 11/2018 |

OTHER PUBLICATIONS

International Search Report and Written Opinion dated May 25, 2018 for International Application No. PCT/US2018/022371.
International Search Report and Written Opinion dated Jun. 15, 2018 for International Application No. PCT/US2018/022377.
International Search Report and Written Opinion dated Aug. 31, 2018 for International Application No. PCT/US2018/030751.
International Search Report and Written Opinion dated Jun. 27, 2019 for International Application No. PCT/US2019/029336.
International Search Report and Written Opinion dated Aug. 16, 2019 for International Application No. PCT/US2019/029345.
International Search Report and Written Opinion dated Nov. 2, 2020 for International Application No. PCT/US2020/046141.

* cited by examiner

MEDICAL DEVICE INCLUDING ATTACHABLE TIP MEMBER

CROSS-REFERENCE TO RELATED APPLICATIONS

This application claims the benefit of priority of U.S. Provisional Application No. 62/887,088 filed Aug. 15, 2019, the entire disclosure of which is hereby incorporated by reference.

TECHNICAL FIELD

The present disclosure pertains to medical devices, and methods for manufacturing medical devices. More particularly, the present disclosure pertains to medical devices including an attachable tip member.

BACKGROUND

A wide variety of intracorporeal medical devices have been developed for medical use, for example, intravascular use. Some of these devices include heart valves, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example system for delivering an implantable heart valve includes an inner shaft having a proximal end region, a distal end region and a first engagement member disposed along a portion of the distal end region and a tip assembly configured to attach to the inner shaft. The tip assembly includes a nosecone having a distal end region and a proximal end region, a second engagement member disposed within at least a portion of the nosecone, the second engagement member including a first locking member, the first locking member configured to deflect from a first position to a second engaged position. Further, attaching the tip assembly to the inner shaft includes deflecting the first locking member such that the locking member is coupled to the first engagement member.

Alternatively or additionally to any of the embodiments above, further comprising a collar disposed along a portion of the second engagement member adjacent the first locking member.

Alternatively or additionally to any of the embodiments above, wherein the first engagement member includes a first shoulder portion, a second shoulder portion and a recessed portion located between the first shoulder portion and the second shoulder portion.

Alternatively or additionally to any of the embodiments above, wherein the recessed portion includes an outer surface, and wherein the outer surface of the recessed portion is positioned radially inward of an outer surface of the first shoulder and an outer surface of the second shoulder.

Alternatively or additionally to any of the embodiments above, wherein the first locking member is configured to be disposed along the outer surface of the recessed portion when in the second engaged position.

Alternatively or additionally to any of the embodiments above, wherein the collar is configured to mask a portion of the second engagement member.

Alternatively or additionally to any of the embodiments above, wherein the second engagement member includes a first lumen extending therein, and wherein the distal end region of the inner shaft is configured to be inserted into the first lumen of the second engagement member.

Alternatively or additionally to any of the embodiments above, wherein the tip assembly includes a longitudinal axis, and wherein engagement of the first shoulder and the first locking member is designed to limit movement of the tip assembly along the longitudinal axis.

Alternatively or additionally to any of the embodiments above, wherein the distal end region of the nosecone includes a tapered portion.

Alternatively or additionally to any of the embodiments above, wherein the second engagement member includes a second locking member spaced circumferentially away from the first locking member, the second locking member configured to deflect from a first position to a second engaged position.

Alternatively or additionally to any of the embodiments above, wherein the second locking member is configured to be disposed along the outer surface of the recessed portion when the second locking member is in the second engaged position.

Alternatively or additionally to any of the embodiments above, wherein the nosecone includes a base portion, the base portion having an outer diameter and a length, and wherein the ratio of the outer diameter of the base portion to the length of the base portion is between 0.5 to 3.0.

Another example system for delivering an implantable heart valve includes an inner shaft having a proximal end region, a distal end region and a first engagement member disposed along a portion of the distal end region. The system also includes a tip member attached to the inner shaft, the tip member including a nosecone having a distal end region and a proximal end region, a second engagement member disposed within at least a portion of the nosecone, the second engagement member including a first locking member and a second locking member, the second locking member spaced circumferentially away from the first locking member. The system also includes a collar disposed along a portion of the second engagement member, wherein the collar is positioned radially outward of both the first locking member and the second locking member. Additionally, both the first locking member and the second locking member are configured to deflect from a first position to a second engaged position and the first locking member and the second locking member attach the tip member to the inner member when in the second engaged position.

Alternatively or additionally to any of the embodiments above, wherein the first engagement member includes a first shoulder portion, a second shoulder portion and a recessed portion located between the first shoulder portion and the second shoulder portion.

Alternatively or additionally to any of the embodiments above, wherein the recessed portion includes an outer surface, and wherein the outer surface of recessed portion is positioned radially inward of an outer surface of the first shoulder and an outer surface of the second shoulder.

Alternatively or additionally to any of the embodiments above, wherein both the first locking member and the second locking member are configured to be disposed along the outer surface of the recessed portion when in the second engaged position.

Alternatively or additionally to any of the embodiments above, wherein the collar is configured to mask a portion of the second engagement member.

Alternatively or additionally to any of the embodiments above, wherein the tip member includes a longitudinal axis, and wherein engagement of the first shoulder with the first locking member and the first shoulder with the second locking member is designed to limit movement of the tip member along the longitudinal axis.

Alternatively or additionally to any of the embodiments above, wherein the nosecone includes a base portion, the base portion having an outer diameter and a length, and wherein the ratio of the outer diameter of the base portion to the length of the base portion is between 0.5 to 3.0.

An example method for delivering an implantable heart valve includes attaching a tip member to an inner catheter of a medical device delivery system, the medical device delivery system including the implantable heart valve, wherein attaching the tip member to the inner catheter includes inserting a first engagement member disposed along a distal end region of the inner catheter into a second engagement member of the tip member, and wherein inserting the first engagement member into the second engagement member includes deflecting at least one locking member disposed along the second engagement member from a first position to a second engaged position. Further, the method includes advancing the medical device delivery system to a target site adjacent the heart and deploying the implantable heart valve at the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
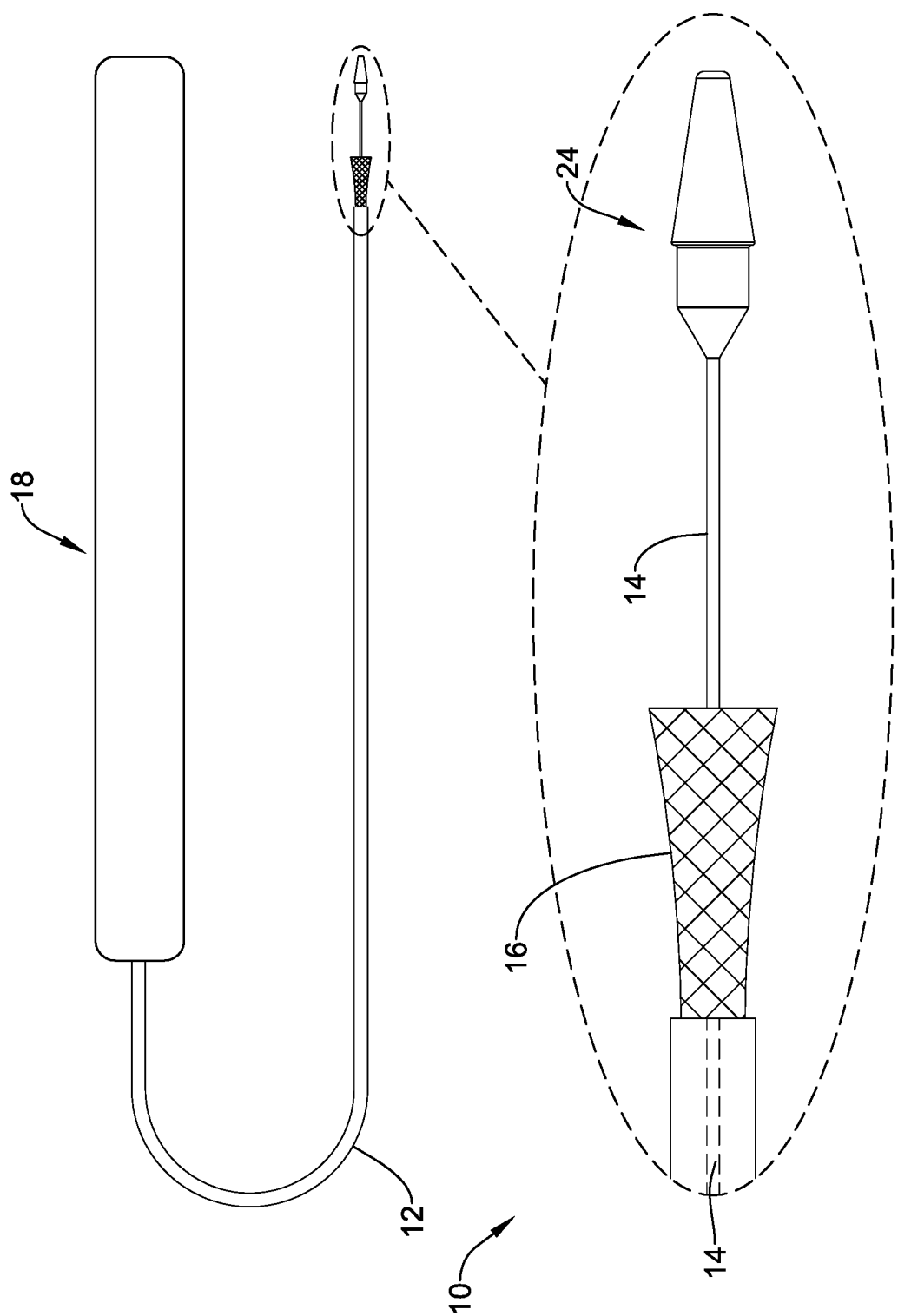
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1, for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 18 may be disposed at a proximal end of the outer sheath 12 and/or the inner catheter 14 and may include one or more actuation mechanisms associated therewith. In other words, a tubular member (e.g., the outer sheath 12, the inner catheter 14, etc.) may extend distally from the medical device handle 18. In general, the medical device handle 18 may be designed to manipulate the position of the outer sheath 12 relative to the inner catheter 14 and/or aid in the deployment of the medical implant 16. Additionally, in some embodiments, such as that illustrated in FIG. 1, the medical device system 10 may include a tip member 24 attached to the distal end of the inner catheter 14.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1, for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 18 in order to translate the medical implant 16 into a generally shortened and larger profile "deployed" configuration suitable for implantation within the anatomy. For example, in some instances the inner catheter (or components thereof) may be coupled to medical implant 16 whereby actuation of the inner catheter 14 relative to the outer sheath 12 and/or the medical implant 16 may deploy the medical device 16 within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system 10 may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

In some instances, it may be desirable to design the medical device system 10 such that the tip member 24 may be unattached to the system 10 when initially packaged (e.g., unattached to the inner catheter 14 when placed in the device packaging prior to a clinician utilizing the device 10 in a medical procedure) whereby the tip member 24 may be subsequently attached to the inner catheter 14 after the packaging containing the medical device system 10 has been opened. Additionally, having the tip member 24 free from the inner catheter 14 prior to the procedure may allow other portions of the medical device system 10 (e.g., the medical implant 16) to be packaged separately and later attached to the medical device system 10 prior to the medical procedure.

Figure 2:
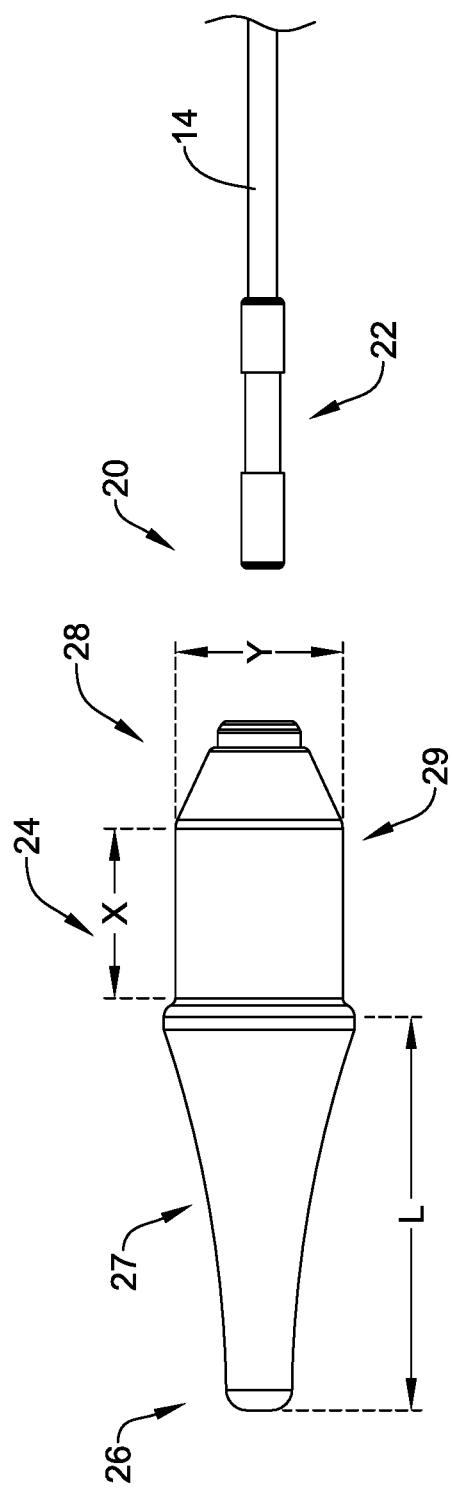
FIG. 2 is a side view of the tip assembly spaced away from the inner shaft of FIG. 1.

FIG. 2 illustrates the tip member 24 spaced away (e.g., unattached) to the inner member 14. The inner member 14 shown in FIG. 2 may be referred to as an inner shaft, inner catheter shaft, inner tubular member, or the like. As can be seen in FIG. 2, the inner member may include a distal end region 20, a proximal end region (not shown in FIG. 2) and a lumen extending therein. The lumen of the inner catheter 14 may be utilized to extend a guidewire (or similar medical device) therein.

FIG. 2 further illustrates that the distal end region 20 of the inner member 14 may further include a first engagement member 22 attached thereto. The first engagement member 22 will be further described in detail below with respect to FIG. 5. As will be described below, the first engagement member 22 may include one or more features which engage with one or more portions of the tip member 24 to securely attach the inner member 14 to the tip member 24.

Additionally, FIG. 2 illustrates that the tip member 24 may include a distal end region 26 and a proximal end region 28. As shown in FIG. 2, the distal end region 26 may include a tapered portion 27. In some examples, the tapered portion 27 may include a length "L," as illustrated in FIG. 2. The length of the tapered portion 27 may be from about 0.10 inches to about 2.50 inches, or about 0.20 inches to about 2.00 inches or from about 0.30 inches to about 1.50 inches. The length of the tapered portion 27 may influence the flexibility of the distal end portion 26 of the tip member 24. In other words, different taper lengths and shapes may determine the flexibility characteristics of the distal end region 26 of the tip member 24.

The tapered portion 27 of the tip member 24 may include a curve, such as the curved tapered portion 27 shown in FIG. 2. However, this is not intended to be limiting. Rather, the tapered portion 27 of the tip member 24 may include a variety of different tapered shapes. For example, the tapered portion 27 may be tapered in substantially straight line. In other examples, the tapered portion 27 may include multiple curves. In yet other examples, the tapered portion 27 may include a combination of straight and curved portions.

FIG. 2 further illustrates that the tip member 24 may include stem portion 29 positioned proximal to the tapered portion 27. The stem portion 29 may include a length "X". Additionally, the stem portion 29 may include an outer diameter "Y." In some examples, the ratio of the length X and the outer diameter Y may be referred to as the "seat and seal ratio." In some instances, the value of the seat and seal ratio (e.g., the ratio of X/Y) may be about 0.5:1 to about 3:1. However, in some examples, it may be desirable to design the tip member 24 to have a seat and seal ratio of about 2:1 because this ratio may provide an adequate seal with the outer sheath 12 while limiting axial movement of the tip member 24 relative to the outer sheath 12. Limiting the axial movement of the tip member 24 relative to the outer sheath 12 may be beneficial during device tracking and positioning.

While not illustrated in FIG. 2, it can be appreciated that, in some examples, the tip member 24 may include an inner lumen extending therein. It can be further appreciated that, in some examples, the inner lumen of the tip member 24 may longitudinally align with the inner lumen of the inner member 14. In other words, in some examples, the lumen of the tip member 24 may align with the lumen of the inner member 14 such that a stylet (discussed below) or similar device may be able to pass through the lumen of the tip member 24 and into the lumen of the inner member 14.

Figure 3:
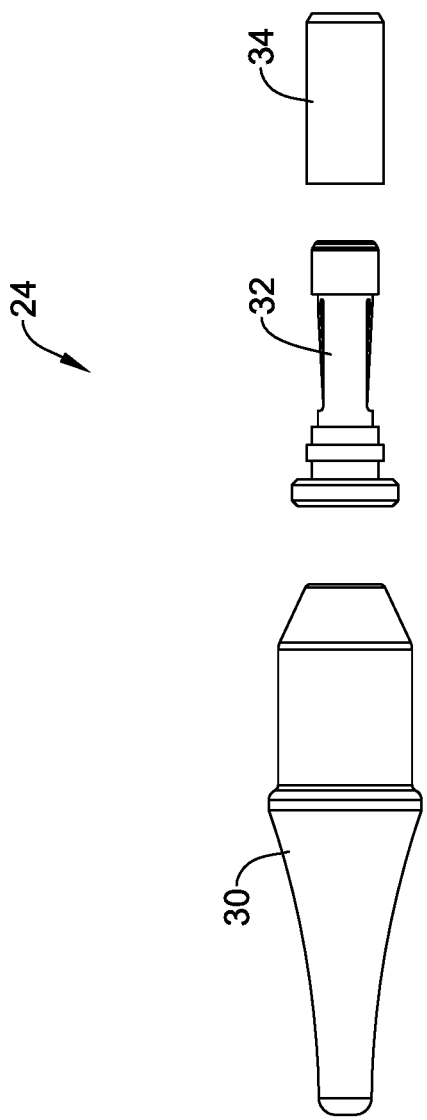
FIG. 3 is an exploded view of the tip assembly and inner shaft shown in FIG. 1.

FIG. 3 illustrates, that in some examples, the tip member 24 may include one or more components which, in combination, form the tip member 24. In other words, in some examples, one or more separate components may be assembled together during a manufacturing process to form the tip member 24 (e.g., tip assembly 24). For example, FIG. 3 illustrates an exploded view of the tip member 24. FIG. 3 illustrates that the tip member 24 may include an outer nosecone 30, a second engagement member 32 and a collar 34.

In some instances, the tip member 24 may be formed by positioning the collar 34 over a portion of the outer surface of the second engagement member 32. Further, after the collar 34 has been positioned over a portion of the outer surface of the second engagement member 23, the nosecone 30 may be over-molded onto the combined second engagement member 32 and collar 34. It can be appreciated that, in some examples, the collar 34 may act as a "mask" which prevents excess polymer material (or other foreign material) from reaching the portions of the second engagement member 32 that are underneath the collar 34. In other words, the order of manufacturing steps may include positioning the collar 34 along the second engagement member 32, followed by over-molding the nosecone over both the second engagement member 32 and the collar 34. Manufacturing the tip member 24 in this manner may permit the collar 34 to prevent foreign matter (polymer material) from reaching the masked portions of the second engagement member 32. The relationship between the nosecone 30, the second engagement member 32 and the collar will be discussed in greater detail below.

Figure 4:
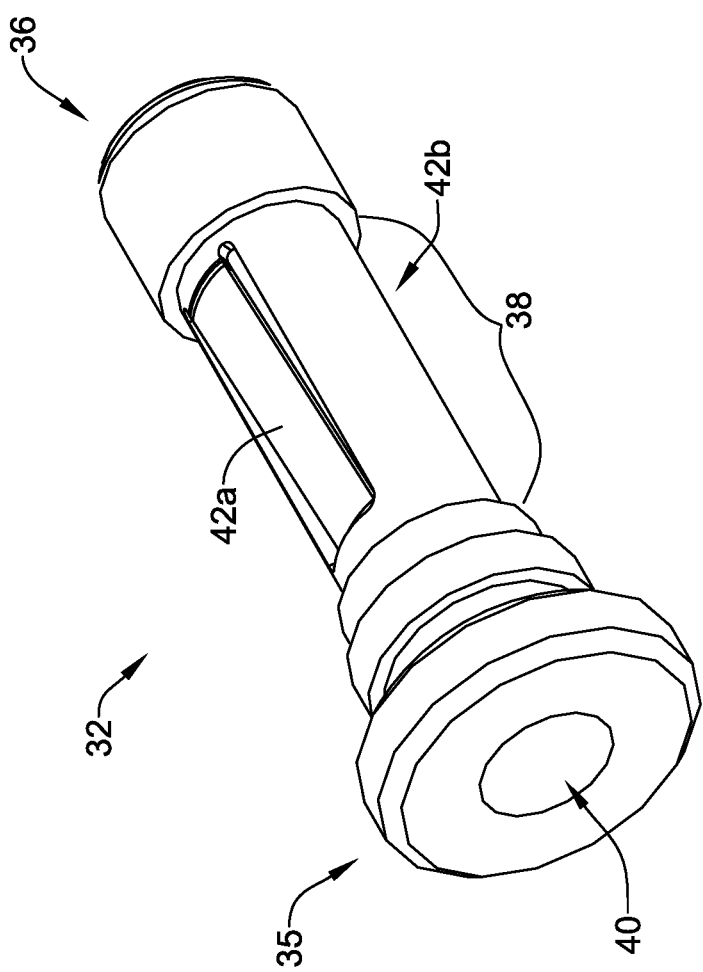
FIG. 4 is a portion of the example medical device of FIG. 1.

FIG. 4 illustrates a perspective view of the second engagement member 32 described above. As shown in FIG. 4, the second engagement member may include a distal end region 35, a proximal end region 36 and a medial region 38 located between the distal end region 35 and the proximal end region 36. Additionally, as described above, the second engagement member 32 may include a lumen 40 extending therein.

Further, as shown in FIG. 4, the medial region 38 of the second engagement member 32 may include a first locking member 42a and a second locking member 42b. It should be noted that the second locking member 42b is not visible in FIG. 4, but it can be appreciated that the second locking member 42b may be positioned 180 degrees from the position of the locking member 42a (e.g., the second locking member 42b may be positioned on the "underside" of the first engagement member 22 as illustrated in FIG. 4). The second locking member 42b may be similar in form and function as the first locking member 42a shown in FIG. 4.

Both of the first locking member 42a and the second locking member 42b may be formed from the wall defining the medial region 38 of the second engagement member 32. For example, each of the locking members 42a/42b may resemble a flap, tab, etc. which may be laser cut from the wall defining the medial region 38 of the second engagement member 32. Additionally, the locking members 42a/42b may be designed to deflect radially inward and outward (e.g., to deflect toward or away from the longitudinal axis of the second engagement member 32). In other words, the second engagement member 32 may be designed such that the locking members 42a/42b can deflect (e.g., pivot, flex, etc.) into the lumen 40 of the second engagement member 32. In some examples, the locking members 42a/42b may be bias radially inward. As will be described in greater detail below, the locking members 42a/42b of the second engagement member 32 may be designed to engage a portion of the first engagement member 22 described above.

Figure 5:
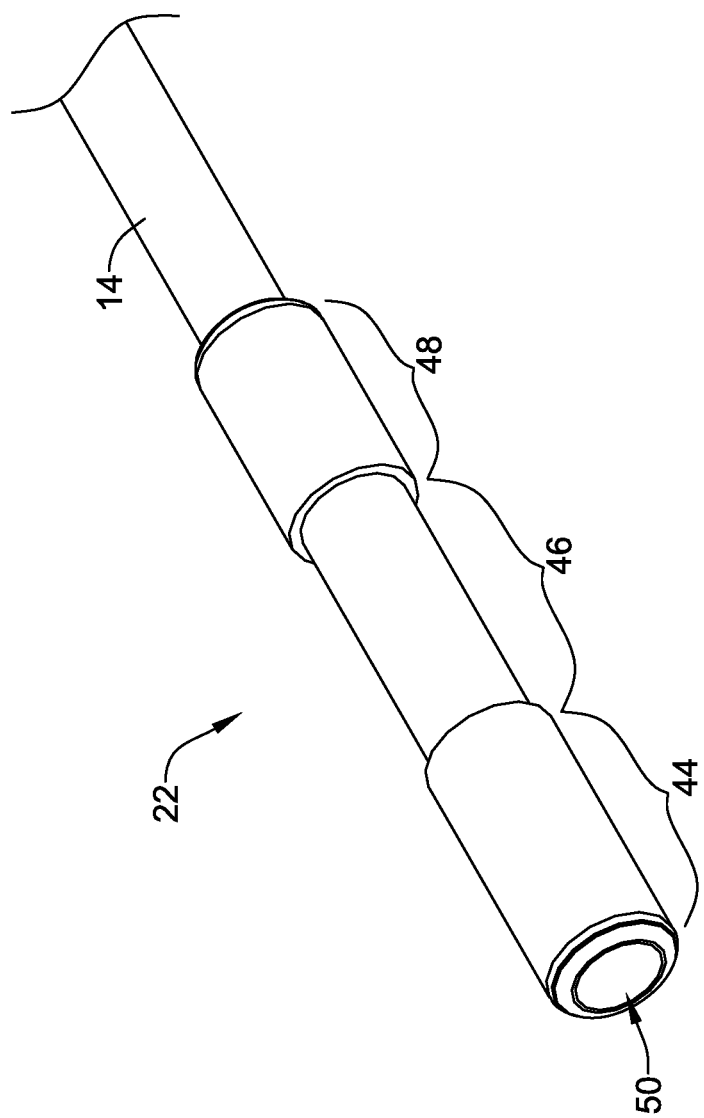
FIG. 5 is a portion of the example medical device of FIG. 1.

FIG. 5 illustrates a perspective view of the first engagement member 22. As shown in FIG. 5, the first engagement member 22 may be coupled (e.g., attached) to the distal end region of the inner catheter 14. As discussed above, the first engagement member 22 may include a lumen 50 extending therein.

Further, as shown in FIG. 5, the first engagement member 22 may include a distal shoulder portion 44, a proximal shoulder portion 48 and a recessed portion 46 located between the distal shoulder portion 44 and the proximal shoulder portion 48. It can be appreciated from FIG. 5 that each of the distal shoulder portion 44 and the proximal shoulder portion 48 may include an outer surface having and outer diameter. It can be further appreciated from FIG. 5 that the recessed portion may include an outer surface which has an outer diameter that is smaller than the outer diameter of the distal shoulder portion 44 and the outer diameter of the proximal shoulder portion 48. In other words, the recessed portion 46 may resemble a channel or groove extending around the circumferentially around the first engagement member 22.

It can be appreciated that one or more of the distal shoulder portion 44, the proximal shoulder portion 48 and the recessed portion 46 may be formed as separate components which are attached to the outer surface of the inner catheter 14. In other words, one or more of the distal shoulder portion 44, the proximal shoulder portion 48 and the recessed portion 46 may be over-molded onto the outer surface of the inner member 14. In some examples, the distal shoulder portion 44 and the proximal shoulder portion 48 may be formed from polymer materials which are over-molded onto a metal component 46. However, this is not intended to be limiting. Rather, it is contemplated that, in some examples, the one or more of the distal shoulder portion 44, the proximal shoulder portion 48 and the recessed portion 46 may be formed as a single component which is attached to the inner catheter 14. Further, in yet other examples, it is contemplated that the distal shoulder portion 44, the proximal shoulder portion 48 and the recessed portion 46 may be formed from the same material as the inner catheter 14. For example, the distal shoulder portion 44, the proximal shoulder portion 48 and the recessed portion 46 may be formed as a monolithic structure with the inner catheter 14. It is also contemplated that, in some examples, each of the distal shoulder portion 44, the proximal shoulder portion 48 and/or the recessed portion may be formed from different materials.

Figure 6:
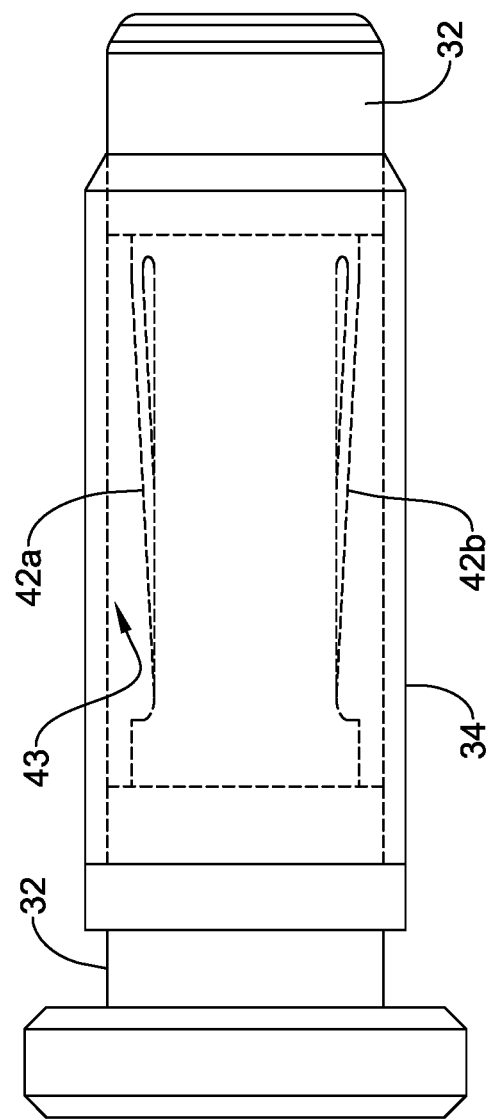
FIG. 6 is a portion of the example medical device of FIG. 1.

FIG. 6 illustrates a side view of the collar 34 (described above with respect to FIG. 3 disposed along a portion of the second engagement member 34. Specifically, FIG. 6 illustrates the collar 34 positioned along the second engagement member 34 such that the collar is adjacent to the locking members 42a/42b (shown in phantom line). Additionally, it can be appreciated that the collar 34 may be positioned radially outward of the locking members 42a/42b. In other words, the collar member 34 may include a lumen through which a portion of the second engagement member 32 extends. Therefore, it can be further appreciated that the inner surface 43 of the collar 34 may define a surface beyond which the locking members 42a/42b cannot extend.

Figure 7:
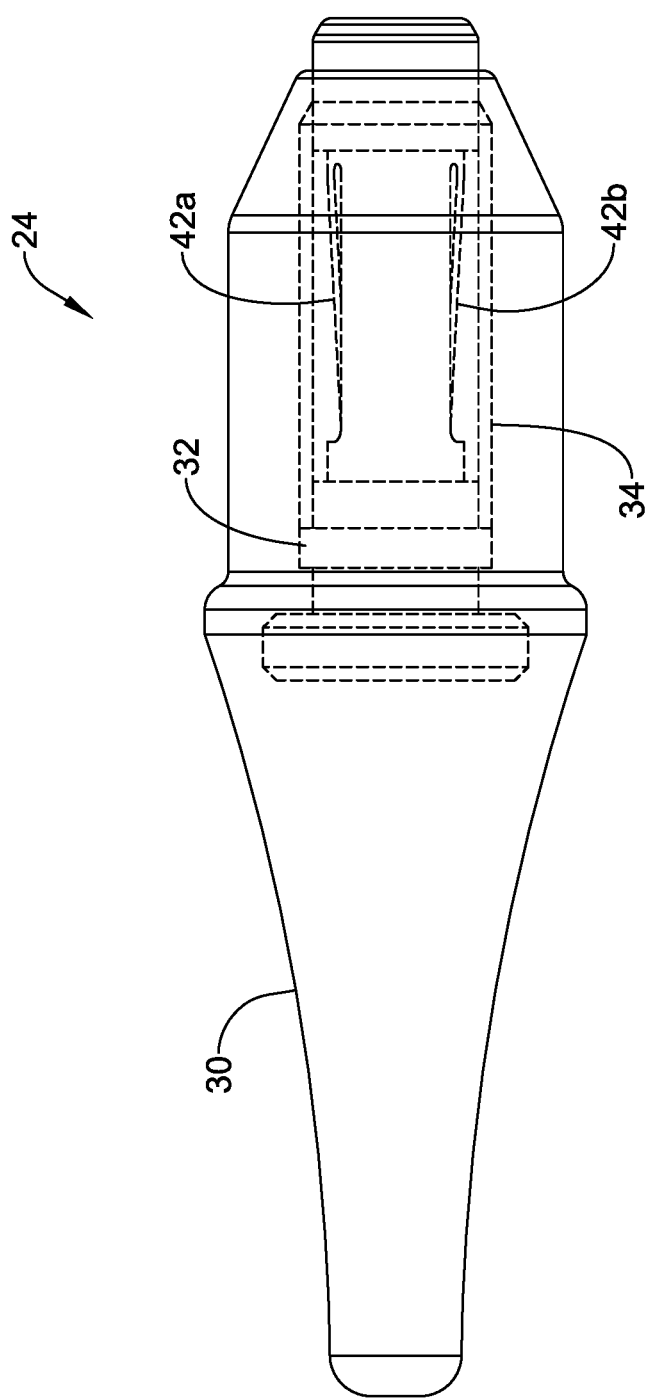
FIG. 7 is a portion of the example medical device of FIG. 1.

FIG. 7 illustrates a side view of the tip member 24 including the nosecone 30 (described above) positioned adjacent to the second engagement member 32 and the collar 34 (the collar being positioned along the second engagement member 32 as described above with respect to FIG. 6). As described above, FIG. 7 illustrates the tip member 24 after the nosecone 30 has been over-molded onto both the second engagement member 32 and the collar 34 (both the second engagement member 32 and the collar 34 are shown in phantom line in FIG. 7). It can be appreciated that over-molding the nosecone 30 onto the second engagement member 32 and the collar 34 may effectively prevent the nosecone 30, the second engagement member 32 and the collar 34 from being separated from one another.

Figure 8:
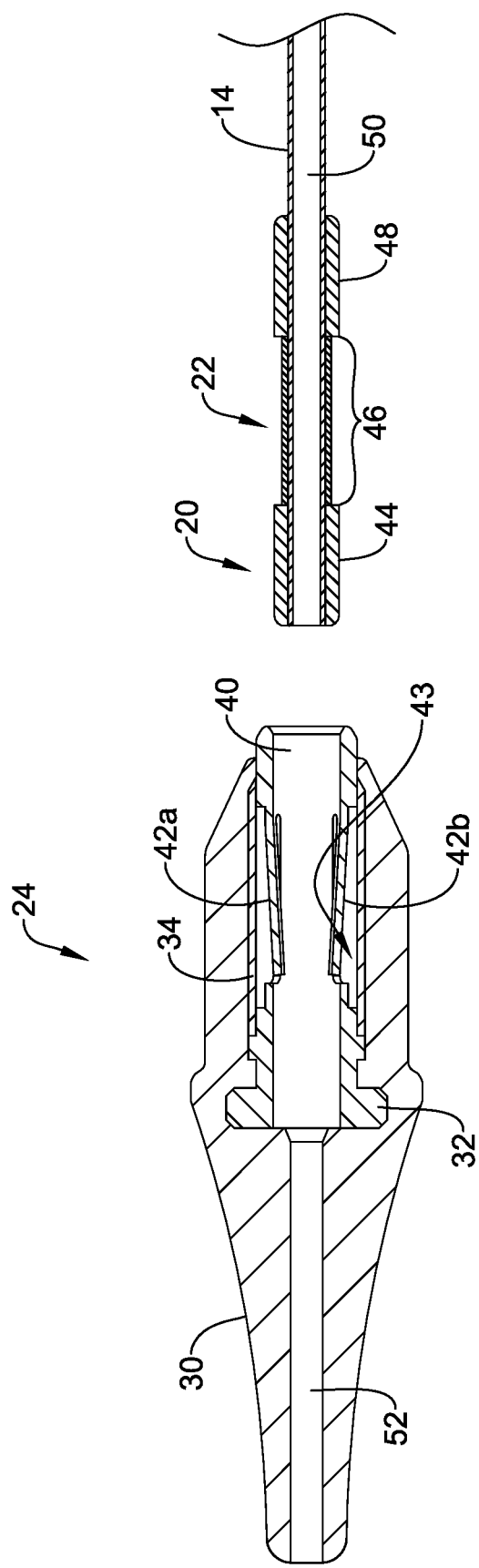
FIG. 8 is a cross-sectional view of a portion of the medical device of FIG. 1 spaced away from the inner shaft.
Figure 9:
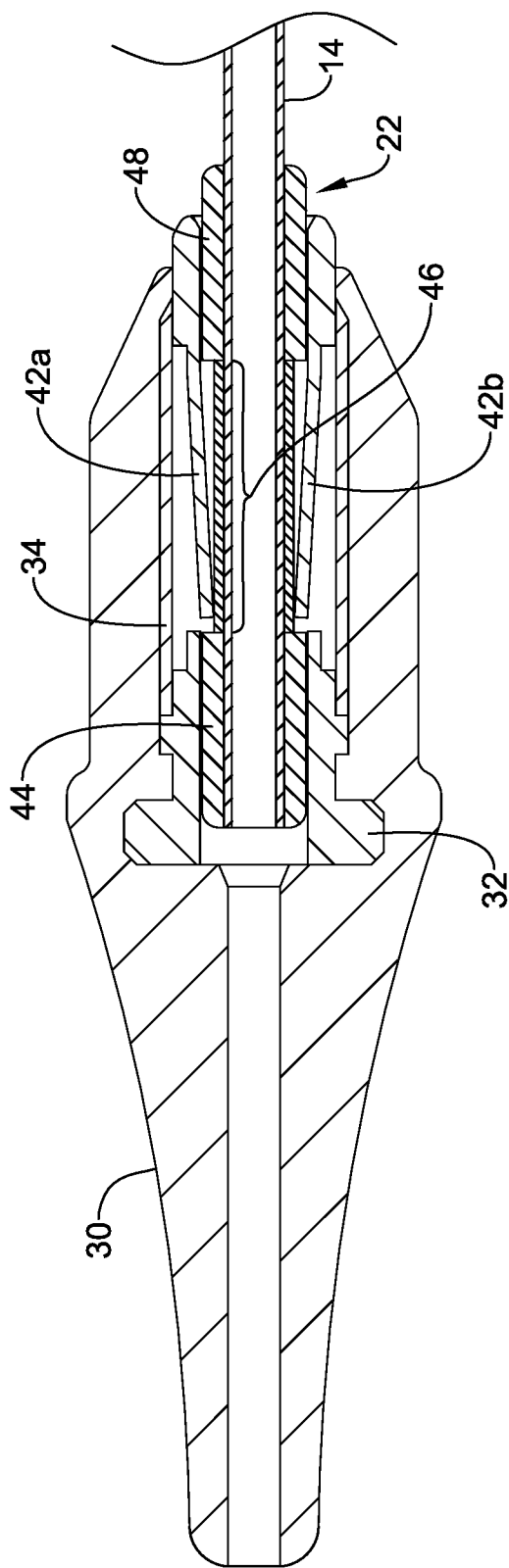
FIG. 9 is a cross-sectional view of the inner shaft after being inserted into the tip assembly of the medical device of FIG. 1.

FIGS. 8 and 9 illustrate two example steps of attaching the inner catheter (including the first engagement member 22) to the tip member 24 (including the nosecone 30, the second engagement member 32 and the collar 34). As described above, it can be appreciated that attaching the inner catheter 14 to the tip member 24 may occur after each of the inner catheter 14, the implantable medical device 16 (shown in FIG. 1) and the tip member 24 are removed from the medical device packaging (e.g., immediately before a medical procedure).

FIG. 8 further illustrates a cross-section of the inner catheter 14 aligned along the longitudinal axis with the tip member 24. As described above, FIG. 8 illustrates that the first engagement member 22 coupled to the distal end region 20 of the inner catheter 14. The first engagement member 22 may include a distal shoulder portion 44, the proximal shoulder portion 48 and the recessed portion 46 extending between the distal shoulder portion 44 and the proximal shoulder portion 48.

Additionally, FIG. 8 illustrates the second engagement member 32 including the locking members 42a/42b. FIG. 8 illustrates the locking members 42a/42b extending radially inward into the lumen 40 of the second engagement member 42. Additionally, as described above, the cross-section of FIG. 8 illustrates the collar 34 positioned adjacent to the locking members 42a/42b, whereby the inner surface 43 of the collar 34 defines a maximum extent for which the locking members 42a/42b may flex radially outward.

FIG. 8 further illustrates that a lumen 52 extending with the distal end region of the nosecone 30. As will discussed in greater detail below, the lumen 52 of the nosecone 30 may be longitudinally aligned with the lumen 40 of the second engagement member 32 and the lumen 50 of the inner catheter 14. The alignment of the lumen 52 of the nosecone 30, the lumen 40 of the second engagement member 32 and the lumen 50 of the inner catheter 14 may permit a stylet or similar device to be position therein.

FIG. 9 illustrates a cross-sectional view of the inner catheter 14 (including the first engagement member 22) after having been inserted into the tip member 24 (including the nosecone 30, the second engagement member 32 and the collar 34 as described above). It can be appreciated from FIG. 9 that inserting the inner catheter 14 into the tip member 24 includes advancing the distal shoulder portion 44 of the first engagement member 22 into the lumen 40 (shown in FIG. 8) of the second engagement member 32. It can be further appreciated that as the inner catheter 14 is further advanced into the second engagement member 32, the distal shoulder portion 44 may deflect the locking members 42a/42b radially outward. Further, as the inner catheter 14 is further advanced into the second engagement member 32, the locking members 42a/42b may align with the recessed portion 46 of the first engagement member, thereby permitting the locking members 42a/42b to deflect radially inward (e.g., "snap into") into the recessed portion 46 of the first engagement member 22 (after the distal shoulder portion 44 advances past the locking members 42a/42b in the distal direction).

It can be appreciated that after the members 42a/42b have deflected into the recessed portion 46 of the first engagement member 22, the tip member 24 may be fixedly attached (e.g., locked) onto the inner catheter 14. In other words, after the locking members 42a/42b have deflected into the recessed portion 46 of the first engagement member 22, the locking members 42a/42b may prevent the distal shoulder portion 44 from shifting in a proximal direction within the second engagement member 32. In other words, if the inner catheter 14 is pulled in a proximal direction after the locking members 42a/42b have deflected into the recessed portion 46 of the first engagement member 22, the locking members 42a/42b may contact the distal shoulder portion 44, thereby preventing the proximal translation thereof.

Figure 10:
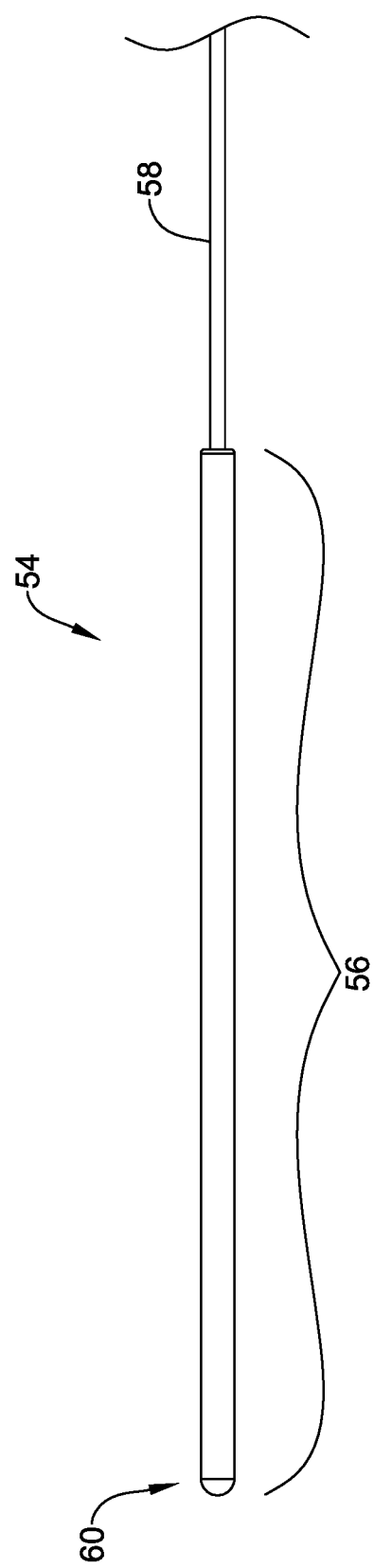
FIG. 10 is side view of an example stylet.

FIG. 10 illustrates an example stylet 54. The stylet 54 may include a distal portion 56 and a proximal portion 58. The stylet 54 may be designed to prevent kinking of the inner catheter 14 when the medical device system 10 is positioned in a package. Further, in some examples, the stylet 54 may be designed to aid in passing the inner catheter 14 through the medical implant 16 (e.g., the heart valve leaflets) when a clinician is attaching the medical implant 16 to the medical device 10 (e.g., in instances in which the medical implant 16 is packaged unattached to the medical device 10). Additionally, the distal end of the distal portion 56 may include a rounded tip 60, which may provide an atraumatic leading surface as the inner catheter 14 is passed through the medical implant 16. In some examples, the length of the distal portion 56 may be about 1.50 inches to 3.50 inches, or about 1.75 inches to about 3.25 inches, or about 2.00 inches to 3.00 inches, or about 2.25 to about 3.75 inches or approximately 2.50 inches.

In some examples, the distal portion 56 of the stylet 54 may be formed as a polymer which is over-molded onto a wire. For example, it can be appreciated that the proximal portion 58 may be a wire member upon which a polymer is over-molded to form the distal portion 56. As illustrated in FIG. 10, the distal portion 56 may include an outer diameter which is greater than the outer diameter of the proximal portion 58.

Figure 11:
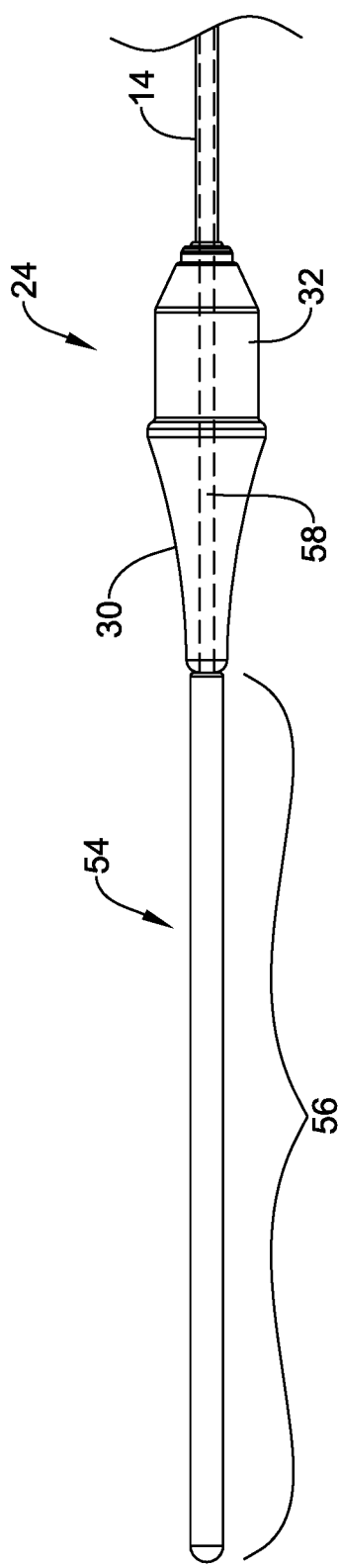
FIG. 11 is a side view of the stylet of FIG. 10 positioned within the medical device of FIG. 1.

FIG. 11 illustrates that stylet 54 engaged with the tip member 24 and the inner member 14. Specifically, FIG. 11 shows the proximal portion 58 of the stylet 54 disposed with the lumen of the nosecone 30, the lumen of the second engagement member 32 and the lumen of the inner catheter 14, as described above. Further, it can be appreciated that the diameter of the proximal portion 58 of the stylet may be sized to provide an interference fit with the lumen of the nosecone 30, the lumen of the second engagement member 32 and/or the lumen of the inner catheter 14. The interference fit of the proximal portion of the stylet may be designed to prevent (or decrease the likelihood) that the stylet may dislodge from the lumen of the nosecone 30, the lumen of the second engagement member 32 and/or the lumen of the inner catheter 14.

It can be appreciated that, in some examples, the flexibility of the distal portion 56 may differ from the flexibility of the proximal portion 58. For example, in some instances the distal portion 56 of the stylet 54 may be stiffer than the proximal portion 58 of the stylet 54. It may be desirable to design the distal portion 56 to have a stiffer flexibility (as compared to the proximal portion 58) because it may allow a user to more easily remove the stylet 54 from the tip member 24 prior to a medical procedure.

Some example materials that can be used for the various components of the medical device system 10 are described herein. However, this is not intended to limit the devices and methods described herein, as the other materials may be utilized for the medical device system 10 and components thereof.

Additionally, medical device system 10 and components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device system 10 and components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 and components thereof to achieve the same result.

In some embodiments, a degree of Magnetic Resonance Imaging (Mill) compatibility is imparted into the shaft. For example, the medical device system 10 and components thereof may include a material that does not substantially distort the image and create substantial artifacts (e.g., gaps in the image). Certain ferromagnetic materials, for example, may not be suitable because they may create artifacts in an MRI image. The medical device system 10 and components thereof may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for delivering an implantable heart valve, comprising:
   an inner shaft having a proximal end region, a distal end region and a first engagement member disposed along a portion of the distal end region; and
   a tip assembly having a longitudinal axis and being configured to attach to the inner shaft, the tip assembly including:
      a nosecone having a distal end region and a proximal end region;
      a second engagement member disposed within at least a portion of the nosecone, the second engagement member including a first locking member, the first locking member having a fixed proximal end, a free distal end, and a length extending therebetween parallel to the longitudinal axis, the first locking member tapering radially inward from the fixed proximal end to the free distal end, the first locking member configured to deflect from a first position to a second engaged position;
   wherein attaching the tip assembly to the inner shaft includes deflecting the first locking member such that the first locking member is coupled to the first engagement member;
   wherein the first engagement member includes a first shoulder portion, a second shoulder portion and a recessed portion located between the first shoulder portion and the second shoulder portion.

2. The system of claim 1, further comprising a collar disposed along a portion of the second engagement member adjacent the first locking member.

3. The system of claim 1, wherein the recessed portion includes an outer surface, and wherein the outer surface of the recessed portion is positioned radially inward of an outer surface of the first shoulder portion and an outer surface of the second shoulder.

4. The system of claim 3, wherein the first locking member is configured to be disposed along the outer surface of the recessed portion when in the second engaged position, thereby fixing the tip assembly to the inner shaft and preventing removal therefrom.

5. The system of claim 4, wherein the collar is configured to mask a portion of the second engagement member.

6. The system of claim 5, wherein the second engagement member includes a first lumen extending therein, and wherein the distal end region of the inner shaft is configured to be inserted into the first lumen of the second engagement member.

7. The system of claim 6, wherein engagement of the first shoulder portion and the first locking member is designed to limit movement of the tip assembly along the longitudinal axis.

8. The system of claim 7, wherein the distal end region of the nosecone includes a tapered portion.

9. The system of claim 8, wherein the second engagement member includes a second locking member having a radially inward distal taper spaced circumferentially away from the first locking member, the second locking member configured to deflect from a first position to a second engaged position.

10. The system of claim 9, wherein the second locking member is configured to be disposed along the outer surface of the recessed portion when the second locking member is in the second engaged position.

11. The system of claim 1, wherein the nosecone includes a base portion, the base portion having an outer diameter and a length, and wherein a ratio of the outer diameter of the base portion to the length of the base portion is between 0.5 to 3.0.

12. A system for delivering an implantable heart valve, comprising:
   an inner shaft having a proximal end region, a distal end region and a first engagement member disposed along a portion of the distal end region;
   a tip member having a longitudinal axis and being configured to be attached to the inner shaft, the tip member including a nosecone having a distal end region and a proximal end region, a second engagement member disposed within at least a portion of the nosecone, the second engagement member including a first locking member having a fixed proximal end, a free distal end, and a length extending therebetween parallel to the longitudinal axis, the first locking member tapering radially inward from the fixed proximal end to the free distal end, and a second locking member having a fixed proximal end, a free distal end, and a length extending therebetween parallel to the longitudinal axis, the second locking member tapering radially inward from the fixed proximal end to the free distal end, the second locking member spaced circumferentially away from the first locking member; and
   a collar disposed along a portion of the second engagement member, wherein the collar is positioned radially outward of both the first locking member and the second locking member;
   wherein both the first locking member and the second locking member are configured to deflect from a first position to a second engaged position;
   wherein the first locking member and the second locking member are configured to fixedly attach the tip member to the inner member when in the second engaged position.

13. The system of claim 12, wherein the first engagement member includes a first shoulder portion, a second shoulder portion and a recessed portion located between the first shoulder portion and the second shoulder portion.

14. The system of claim 13, wherein the recessed portion includes an outer surface, and wherein the outer surface of recessed portion is positioned radially inward of an outer surface of the first shoulder portion and an outer surface of the second shoulder portion.

15. The system of claim 14, wherein both the first locking member and the second locking member are configured to be disposed along the outer surface of the recessed portion when in the second engaged position.

16. The system of claim 15, wherein the collar is configured to mask a portion of the second engagement member.

17. The system of claim 16, wherein engagement of the first shoulder portion with the first locking member and the first shoulder portion with the second locking member is designed to limit movement of the tip member along the longitudinal axis.

18. The system of claim 17, wherein the nosecone includes a base portion, the base portion having an outer diameter and a length, and wherein a ratio of the outer diameter of the base portion to the length of the base portion is between 0.5 to 3.0.

19. A method for delivering an implantable heart valve, the method comprising:
   attaching a tip member to an inner catheter of a medical device delivery system, the medical device delivery system including the implantable heart valve;
   wherein attaching the tip member to the inner catheter includes inserting a first engagement member disposed along a distal end region of the inner catheter into a second engagement member of the tip member, the second engagement member including at least a first locking member having a fixed proximal end, a free distal end and a length extending therebetween parallel to a longitudinal axis of the tip member, the first locking member tapering radially inward from the fixed proximal end to the free distal end, and wherein inserting the first engagement member into the second engagement member includes deflecting at least the first locking member from a first position to a second engaged position thereby fixedly locking the tip member to the inner catheter and preventing removal therefrom;
   wherein the first engagement member includes a first shoulder portion, a second shoulder portion and a recessed portion located between the first shoulder portion and the second shoulder portion,
   advancing the medical device delivery system to a target site adjacent a heart;
   deploying the implantable heart valve at the target site.

* * * * *